United States Patent
Dongare et al.

(10) Patent No.: US 6,791,000 B2
(45) Date of Patent: Sep. 14, 2004

(54) PROCESS FOR VAPOR PHASE NITRATION OF BENZENE USING NITRIC ACID OVER MOLYBDENUM SILICA CATALYST

(75) Inventors: Mohan Keraba Dongare, Pune (IN); Pratap Tukaram Patil, Pune (IN); Kusum Madhukar Malshe, Pune (IN)

(73) Assignee: Council of Scientific and Industrial Research, New Delhi (IN)

( * ) Notice: Subject to any disclaimer, the term of this patent is extended or adjusted under 35 U.S.C. 154(b) by 0 days.

(21) Appl. No.: 10/449,718

(22) Filed: May 30, 2003

(65) Prior Publication Data

US 2004/0024267 A1 Feb. 5, 2004

(30) Foreign Application Priority Data

Jul. 31, 2002 (IN) ............................................. 798/2002

(51) Int. Cl.$^7$ .......................................... C07C 205/06
(52) U.S. Cl. ..................................................... 568/939
(58) Field of Search .......................................... 568/939

(56) References Cited

U.S. PATENT DOCUMENTS 4,551,568 A * 11/1985 Sato et al. .................. 568/939

OTHER PUBLICATIONS

Database CAPLUS on STN, Acc. No. 1994:607985, Yoo et al., Applied Catalysis, A: General (1994), 117(1), pp. 1–16 abstract.*

Database CAPLUS on STN, Acc. No. 1998:755068, Sato et al., Applied Catalysis, A: General (1998), 174(1–2), pp. 77–81 (abstract).*

* cited by examiner

Primary Examiner—Brian J. Davis
(74) Attorney, Agent, or Firm—Ladas & Parry

(57) ABSTRACT

Nitration of benzene is an important reaction for the production of nitro benzene, which is an important intermediate in chemical and pharmaceutical industries. Conventionally nitrobenzene is produced by liquid phase reactions employing mixed acids. A sulfuric acid/nitric acid mixture is the most commonly used nitrating agent. Generation of large amount dilute sulfuric acid, organic wastes and products of their neutralization makes the benzene nitration a environmentally harmful process. The present process enables the preparation of nitrobenzene by vapor phase nitration of benzene over solid acid catalyst, $MoO_3/SiO_2$ using nitric acid. This process is a clean and environment friendly process without use of sulphuric acid.

21 Claims, No Drawings

PROCESS FOR VAPOR PHASE NITRATION OF BENZENE USING NITRIC ACID OVER MOLYBDENUM SILICA CATALYST

FIELD OF THE INVENTION

The present invention relates to a process for vapor phase nitration of benzene using nitric acid over molybdenum silica catalyst. The invention particularly relates to a process for the preparation of mono-nitrobenzene wherein the nitration of benzene is carried out in vapor phase using molybdenum silica catalyst and nitric acid. By the process of present invention nitrobenzene has been prepared in high yield in a continuous process without any waste byproduct formation making it an environment friendly process.

BACKGROUND OF THE INVENTION

Major part of nitrobenzene (95% or more) produced is converted to aniline, which has hundreds of downstream products. Nitrobenzene also is used as a processing solvent in specific chemical reactions. Conventionally nitrobenzene is produced by liquid phase reactions employing mixed acids. A sulfuric acid/nitric acid mixture is the most commonly used nitrating agent. Generation of large amount dilute sulfuric acid, organic wastes and products of their neutralization makes the benzene nitration one of the most environmentally harmful processes.

Vapor-phase nitration of benzene to nitrobenzene over zeolite is expected to be a clean process without sulfuric acid waste. A number of heterogeneous catalysts have been proposed for this process.

In the prior art, vapor phase nitration of aromatic compounds, benzene and toluene at temperature ranging from about 275° C. to about 310° C. is described in McKee and Wilhelm, Industrial and Engineering Chemistry, 28(6), 662–667 (1936) and U.S. Pat. No. 2,109,873. McKee and Wilhelm catalyzed their reaction with silica gel. Bauxite and alumina were reported to be ineffective as catalyst in the vapor phase nitration of benzene.

U.S. Pat. No. 2,431,585 describes vapor phase nitration of aromatic hydrocarbons at temperature from 130° C. to 430° C., using metal phosphates of calcium, iron, magnesium and solid supported phosphoric acid catalysts.

U.S. Pat. No. 4,551,568 describes the vapor phase nitration of benzene over solid mixed oxide catalyst comprising $WO_3$ and $MoO_3$, which exhibited a fairly high and stable activity.

U.S. Pat. No. 3,966,830, Jpn. Pat. No. 58-157748 and U.S. Pat. No. 4,426,543 describe the nitration of aromatics using zeolite catalysts. The lower conversion of benzene to nitrobenzene and faster deactivation of zeolite catalysts are the drawbacks of these processes for commercial application.

U.S. Pat. No. 5,030,776 describes a process for nitrating benzene using nitric acid as a nitrating agent under continuous or intermittent feeding of sulfuric acid as a catalyst on a solid carrier. Vapor phase nitration of benzene has been claimed in U.S. Pat. No. 5,004,846 wherein nitric acid is used as a nitrating agent and a composite oxide or acidic sheet clay mineral ion exchanged with polyvalent metal as a catalyst.

PCT International Patent Application No. WO 96/36587 describes a solvent free process for the nitration of aromatic compounds in which the aromatic compound is reacted with nitric acid in presence of an acid anhydride wherein the process is catalyzed by an aluminosilicate catalyst. Nitric acid and acid anhydride react with each other in-situ to form acyl nitrate and this acts as a nitrating agent for aromatic compounds. For example benzene, naphthalene, anthracene, toluene etc. are nitrated to mononitrated compounds. A mixture of ortho-, meta-, and para-nitrotoluenes is obtained which is then distilled at a pressure of 30 mmHg and a temperature of 30° C. to remove acetic acid as a byproduct.

These prior art processes for the vapor phase nitration of benzene for the preparation of nitrobenzene have the limitations of low conversions low space-time yield, low yield, short catalyst life, contamination of the products by undesirable by-products and the complicated nature of catalysts. These prior art processes use concentrated nitric acid as nitrating agent, which leads to the oxidation products deactivating the catalyst.

OBJECTS OF THE INVENTION

The main object of the present invention is to provide a process for vapor phase nitration of benzene using nitric acid and over molybdenum silica catalyst.

Another object of the present invention is use of ethyl silicate-40 as silica source for the preparation of high surface area $MoO_3/SiO_2$ catalyst.

Yet another object of the present invention is the use of $xMoO_3:(1-x)\ SiO_2$ catalyst, where x=0.05–0.2, preferably x=0.2 for vapor phase nitration of benzene using nitric acid and over molybdenum silica catalyst.

It is another object of the invention to provide a process for the nitration of benzene which is simple and easy to scale up.

It is yet another object of the invention to provide a process for the nitration of benzene which avoids the use of sulphuric acid.

It is another object of the invention to provide a process for the nitration of benzene which uses easily separable solid catalyst with negligible deactivation and long life.

It is a further object of the invention to provide a process for the nitration of benzene which enables good conversion (more than 80%) and 100% selectivity for nitrobenzene.

SUMMARY OF THE INVENTION

Accordingly the present invention provides a process for the vapor phase nitration of benzene, which comprises nitrating benzene with nitric acid over a molybdenum silica catalyst and separating the desired product.

In one embodiment of the invention, benzene is nitrated with nitric acid in the presence of a carrier gas comprising an inert gas.

In another embodiment of the invention, the nitration is carried out in a conventional downflow reactor containing inert ceramic packing as preheater.

In another embodiment of the invention, the molybdenum silica catalyst comprises a granulated molybdenum silica catalyst of composition $MoO_3:(1-x)\ SiO_2$, wherein x=0.05–0.2.

In another embodiment of the invention, the catalyst is used without a promoter.

In another embodiment of the invention, the catalyst is used with a promoter comprising 0.5–2% of a transition metal oxide.

In another embodiment of the invention, the nitration is carried out at a temperature in the range of 100–250° C. and at a reactant weight hourly space velocity (WHSV) in the range of 0.1 to 1.0.

In another embodiment of the invention, resulting product is condensed and then washed with alkali to obtain the desired product.

In another embodiment of the invention, the catalyst used is in the form of a pellet.

In another embodiment of the invention, the mesh size of granulated molybdenum silica catalyst used is in the range of −10 to +20 mesh size.

In another embodiment of the invention, the catalyst used is $MoO_3:(1-x) SiO_2$ where x is 0.2.

In another embodiment of the invention, the $MoO_3/SiO_2$ catalyst used is in amorphous or crystalline form.

In another embodiment of the invention, the molybdenum silica catalyst is in amorphous form.

In another embodiment of the invention, the molybdenum silica catalyst is used along with a promoter comprising 1–2% transition metal oxides selected from the group consisting of $Fe_2O_3$, $CuO$, $NiO$ and $Co_3O_4$.

In another embodiment of the invention, the promoter is $Fe_2O_3$.

In another embodiment of the invention, the nitric acid used is 10 to 70% nitric acid.

In another embodiment of the invention, the molar ratio of nitric acid to benzene is in the range of 4:1 to 1:4.

In another embodiment of the invention, the ratio of nitric acid to benzene is 1:2.

In another embodiment of the invention, the nitration is carried out at a temperature in the range of 120–200° C.

In another embodiment of the invention, the inert gas used is selected from the group consisting of nitrogen, helium and argon.

In another embodiment of the invention, the reactant weight hourly space velocity used is in the range of 0.15 to 0.5.

The present invention also provides a process for vapor phase nitration of benzene using nitric acid over molybdenum silica catalyst which comprises reacting benzene with nitric acid along with an inert gas as carrier gas in a conventional downflow reactor containing inert ceramic packing as preheater and granulated molybdenum silica catalyst of composition $MoO_3:(1-x) SiO_2$, where x=0.05–0.2 at a temperature in the range of 100–250° C., at a reactant weight hourly space velocity (WHSV) in the range 0.1 to 1.0, condensing the resultant product followed by washing with alkali to obtain desired product.

DETAILED DESCRIPTION OF THE INVENTION

The present invention provides a process for the vapor phase nitration of benzene, which comprises nitrating benzene with nitric acid over a molybdenum silica catalyst and separating the desired product.

The process for vapor phase nitration of benzene using nitric acid over molybdenum silica catalyst comprises reacting benzene with nitric acid along with an inert gas as carrier gas in a conventional downflow reactor containing inert ceramic packing as preheater and granulated molybdenum silica catalyst of composition $MoO_3:(1-x) SiO_2$, where x=0.05–0.2 at a temperature in the range of 100–250° C., at a reactant weight hourly space velocity (WHSV) in the range 0.1 to 1.0, condensing the resultant product followed by washing with alkali to obtain desired product. The catalyst is used in the form of a pellet.

The mesh size of granulated molybdenum silica catalyst is in the range of −10 to +20 mesh size. The catalyst used is $MoO_3:(1-x) SiO_2$ where x is 0.2 and can be used in either in amorphous or crystalline form, preferably in amorphous form.

The reaction is carried out in the presence of a promoter comprising 0.5–2%, preferably 1–2% transition metal oxide selected from the group consisting of $Fe_2O_3$, $CuO$, $NiO$ and $Co_3O_4$, preferably $Fe_2O_3$.

The nitric acid used is 10 to 70% nitric acid and the molar ratio of nitric acid to benzene used is 4:1 to −1:4, preferably 1:2

The nitration is carried out at a temperature preferably in the range of 120–200° C. and at a reactant weight hourly space velocity used is preferably in the range of 0.15 to 0.5.

Inert gas is used as a carrier gas selected from the group consisting of nitrogen, helium and argon.

The novelty of the present invention lies in the use of $xMoO_3:(1-x) SiO_2$ catalyst with or without promoter for vapour phase nitration of benzene in high yield and selectivity for nitrobenzene.

The present invention is described in further detail with reference to the examples, which are given by way of illustration only and therefore should not be construed to restrict the scope of the invention.

EXAMPLE 1

$MoO_3/SiO_2$ catalyst used in the present invention was prepared using ammonium molybdate (AR Grade, Loba make) as molybdenum source and ethyl silicate-40 (CAS Registry no. 18594-71-7, supplied by Chemplast) as silica source. 35.28 g of ammonium molybdate [$(NH_4)_6Mo_7O_{24}4H_2O$] was dissolved in 150 ml hot distilled water and added drop wise to the solution of 120 g ethyl silicate-40 in 50 ml isopropyl alcohol with constant stirring. The resulting greenish gel was air dried, ground and calcined at 500° C. in air in a muffle furnace. The catalyst was characterized using XRD, surface area using BET, chemical analysis by AAS and XRF. XRD showed amorphous nature of the catalyst and BET showed the surface area of 372 $m^2/g$. The molar composition of the catalyst was 0.2 $MoO_3$:0.8 $SiO_2$. Molar composition of the $xMoO_3:(1-x) SiO_2$ catalyst was varied where x=0.05–0.2. The catalyst was molded in the form of a pellet, which is granulated to −10 to +20 mesh size for its use in nitration reaction.

EXAMPLE 2

$Fe_2O_3/MoO_3/SiO_2$ catalyst used in the present invention was prepared using ammonium molybdate (AR Grade, Loba make) as molybdenum source, ferric nitrate (SD fine) as iron source and ethyl silicate-40 (CAS registry no. 18594-71-7, supplied by Chemplast) as silica source. 5.65 g. of ferric nitrate was dissolved in 100 ml of isopropyl alcohol which was added to a solution 118.9 g of ethylsilicate-40 in 100 ml of isopropyl alcohol under constant stirring. 35.28 g of ammonium molybdate [$(NH_4)_6Mo_7O_{24}.4H_2O$] was dissolved in 150 ml hot distilled water and was added drop wise to the above solution with constant stirring. The resulting reddish gel was air dried, ground and calcined at 500° C. in air in a muffle furnace. The catalyst was characterized using XRD, surface area using BET, chemical analysis by AAS and XRF. The molar composition of the catalyst was 0.007 $F_2O_3$:0.2 $MoO_3$:0.793 $SiO_2$. The catalyst was molded in the form of a pellet, which is granulated to −10 to +20 mesh size for its use in nitration reaction.

Similarly $CuO$, $NiO$, $Co_3O_4$ containing $MoO_3/SiO_2$ catalysts were prepared by using respective metal nitrates and the molar composition was maintained $xMO/0.2MoO_3/0.793SiO_2$ where x was 0.05 to 0.2 moles of respective metal oxides.

EXAMPLE 3

10 g of catalyst prepared by the procedure given in the Example 1 was loaded in a tubular glass reactor of 15 mm diameter and 25 mm length. The upper part of the reactor was packed with inert ceramic beads as preheating zone. Benzene and nitric acid (70%) were fed to the reactor using syringe pumps. Reaction conditions were as follows.
Reaction temperature=120° C.
Carrier gas=$N_2$
Benzene/$HNO_3$=1.4:1 (molar ratio)
WHSV (benzene)=0.17

The product was condensed at 9° C. and collected in a receiver. The product was analyzed by gas chromatography. Results after 25 hours from beginning of reaction are shown below.
Conversion of benzene=68.0%
Yield for nitrobenzene=68.0%
Selectivity of nitrobenzene=100%

There was negligible deactivation in catalyst activity and selectivity during this period.

EXAMPLE 4

Example 3 was repeated except increasing the Weight Hourly Space Velocity (WHSV) to 0.34. Reaction conditions were as follows.
Reaction temperature=120° C.
Carrier gas=$N_2$
Benzene/$HN_{O3}$=1.4:1 (molar ratio)
WHSV=0.34

Results after 81 hours from beginning of reaction are shown below.
Conversion of benzene=63.4%
Yield for nitrobenzene=62.77%
Selectivity of nitrobenzene=99.8%
There was no deactivation in the activity and selectivity of the catalyst during this period.

EXAMPLE 5

Example 3 was repeated except that benzene/$HNO_3$ ratio was changed. The reaction conditions were as follows.
Reaction Temperature=120° C.
Carrier gas=$N_2$
Benzene/$HNO_3$=1.6:1 (molar ratio)
WHSV=0.17

Results after 25 hours from beginning of reaction are shown below.
Conversion of benzene=56.2%
Yield for nitrobenzene=55.75%
Selectivity of nitrobenzene=99.2%
There was no deactivation in the catalyst activity and selectivity during this period.

EXAMPLE 6

The catalyst prepared as per Example-1, further calcined at 600° C. and was characterized by XRD and BET surface area measurements. The XRD showed the presence of crystalline form $MoO_3$ and amorphous form of silica. The surface area of the catalyst was 215 $m^2$/g. The catalyst was molded in the form of a pellet, which is granulated to −10 to +20 mesh size for its use in nitration. The nitration reaction was carried out as mentioned in the Example 2. The reaction conditions were as follows.
Reaction temperature=120° C.
Carrier gas=$N_2$
Benzene/$HNO_3$=1.4:1 (molar ratio)
WHSV=0.17

Results after 25 hours from beginning of reaction are shown below.
Conversion of benzene=48.56%
Yield for nitrobenzene=47.8%
Selectivity of nitrobenzene=98.5%
There was no deactivation in the activity and selectivity of the catalyst during this period.

EXAMPLE 7

Example 3 was repeated except that temperature of the reaction was changed. The reaction conditions were as follows.
Reaction Temperature=180° C.
Carrier gas=$N_2$
Benzene/$HNO_3$=1.4:1 (molar ratio)
WHSV=0.17

Results after 25 hours from beginning of reaction are shown below.
Conversion of benzene 50.2%
Yield for nitrobenzene=49.7%
Selectivity of nitrobenzene=99.0%
No deactivation of the catalyst was seen during this period.

EXAMPLE 8

Example 3 was repeated except that the catalyst with 0.7 mol % $Fe_2O_3$ prepared as per example 2. The reaction conditions were as follows.
Reaction Temperature=120° C.
Carrier gas=$N_2$
Benzene/$HNO_3$=1.4:1 (molar ratio)
WHSV=0.17

Results after 25 hours from beginning of reaction are shown below.
Conversion of benzene=75%
Yield for nitrobenzene=75%
Selectivity of nitrobenzene=100%
No deactivation of the catalyst was seen during this period.

Advantages of the Invention a) No use of sulphuric acid b) Solid acid catalyst easy for separation and use c) Negligible deactivation of catalyst, long life of catalyst d) A good conversion (more than 80%) and 100% selectivity for nitrobenzene.

e) Ease of operation and scale up.

We claim:

1. A process for the vapor phase nitration of benzene, which comprises nitrating benzene with nitric acid over a molybdenum silica catalyst and separating the desired product.

2. A process as claimed in claim 1 wherein benzene is nitrated with nitric acid in the presence of a carrier gas comprising an inert gas.

3. A process as claimed in claim 1 wherein the nitration is carried out in a conventional downflow reactor containing inert ceramic packing as preheater.

4. A process as claimed in claim 1 wherein the molybdenum silica catalyst comprises a granulated molybdenum silica catalyst of composition $MoO_3$:(1−x) $SiO_2$, wherein x=0.05–0.2.

5. A process as claimed in claim 1 wherein the catalyst is used without a promoter.

6. A process as claimed in claim 1 wherein the catalyst is used with a promoter comprising 0.5–2% of a transition metal oxide.

7. A process as claimed in claim 1 wherein the nitration is carried out at a temperature in the range of 100–250° C. and at a reactant weight hourly space velocity (WHSV) in the range of 0.1 to 1.0.

8. A process as claimed in claim 1 wherein the resulting product is condensed and then washed with alkali to obtain the desired product.

9. A process as claimed in claim 1 wherein the catalyst used is in the form of a pellet.

10. A process as claimed in claim 4, wherein the mesh size of granulated molybdenum silica catalyst used is in the range of −10 to +20 mesh size.

11. A process as claimed in claims 1, wherein the catalyst used is $MoO_3:(1-x) SiO_2$ where x is 0.2.

12. A process as claimed in claims 1, wherein the $MoO_3/SiO_2$ catalyst used is in amorphous or crystalline form.

13. A process as claimed in claim 12 wherein the molybdenum silica catalyst is in amorphous form.

14. A process as claimed in claim 1 wherein the molybdenum silica catalyst is used along with a promoter comprising 1–2% transition metal oxides selected from the group consisting of $Fe_2O_3$, CuO, NiO and $Co_3O_4$.

15. A process as claimed in claim 14 wherein the promoter is $Fe_2O_3$.

16. A process as claimed in claim 1, wherein the nitric acid used is 10 to 70% nitric acid.

17. A process as claimed in claim 1, wherein the molar ratio of nitric acid to benzene is in the range of 4:1 to 1:4.

18. A process as claimed in claim 17 wherein the ratio of nitric acid to benzene is 1:2.

19. A process as claimed in claim 1, wherein the nitration is carried out at a temperature in the range of 120–200° C.

20. A process as claimed in claim 2, wherein the inert gas used is selected from the group consisting of nitrogen, helium and argon.

21. A process as claimed in claim 7, wherein the reactant weight hourly space velocity used is in the range of 0.15 to 0.5.

\* \* \* \* \*

UNITED STATES PATENT AND TRADEMARK OFFICE
CERTIFICATE OF CORRECTION

PATENT NO.    : 6,791,000 B2
DATED         : September 14, 2004
INVENTOR(S)   : Mohan Keraba Dongare et al.

It is certified that error appears in the above-identified patent and that said Letters Patent is hereby corrected as shown below:

<u>Title page,</u>
Item [30], Foreign Application Priority Data, "798/2002" should read
-- 798/DEL/2002 --.

Signed and Sealed this

Fifth Day of April, 2005

JON W. DUDAS
*Director of the United States Patent and Trademark Office*